United States Patent [19]
Kosti

[11] Patent Number: 5,846,522
[45] Date of Patent: Dec. 8, 1998

[54] FLUORIDATION AND REFLUORIDATION OF WATER BASED COMPOSITIONS

[76] Inventor: Carl Kosti, 4503 Williamsburg Rd. NW., Cincinnati, Ohio 45215

[21] Appl. No.: 984,292

[22] Filed: Dec. 3, 1997

Related U.S. Application Data

[63] Continuation-in-part of Ser. No. 600,852, Feb. 13, 1996, abandoned.

[51] Int. Cl.$^6$ ............................... A61K 7/18; A61K 33/16
[52] U.S. Cl. .......................... 424/52; 210/416.3; 210/753; 424/52; 424/673; 424/674; 424/676; 426/74; 426/590
[58] Field of Search ........................ 424/52, 673; 426/74, 426/590; 210/416.3, 753

[56] References Cited

U.S. PATENT DOCUMENTS

| | | | |
|---|---|---|---|
| 5,037,639 | 8/1991 | Tung | 424/57 |
| 5,268,167 | 12/1993 | Tung | 424/52 |
| 5,437,857 | 8/1995 | Tung | 424/52 |
| 5,460,803 | 10/1995 | Tung | 424/57 |
| 5,534,244 | 7/1996 | Tung | 424/52 |
| 5,562,895 | 10/1996 | Tung | 424/57 |
| 5,683,678 | 11/1997 | Heckert et al. | 424/52 |

*Primary Examiner*—Shep K. Rose
*Attorney, Agent, or Firm*—R. William Graham

[57] ABSTRACT

A bottled fluoridated water based drinking composition for the prevention and control of dental decay includes in a substantially non-fluoride reactive bottle containing therein at least one additional fluoride compound selected from a group consisting essentially sodium fluoride, potassium fluoride, magnesium fluoride, calcium fluoride, stannous fluoride, sodium monofluorophosphate, potassium monofluorophosphate and hydrogen fluoride and physiologically acceptable salts thereof, an acidifying compound which when dissolved in water will provide a weak acid and a weak base to initiate a buffering action and prevent the fluoride ions from going to completion and other selected formulating agents to provide protection of tooth surfaces from tooth caries disease and eventual tooth loss.

6 Claims, 2 Drawing Sheets

◎ Inorganic Substances

○ Organic Substances

− + Ionized Substances

△ Fluoride Removed from Untreated Water

▲ Fluoride Added to Purified Water

FLUORIDATION AND REFLUORIDATION OF WATER BASED COMPOSITIONS

This is a continuation in part of U.S. Ser. No. 08/600,852 filed Feb. 13, 1996 now abandoned.

BACKGROUND OF THE INVENTION

FIELD OF THE INVENTION

This invention relates to novel methods of fluoridating or refluoridating water and other liquids and fluoridated water based compositions formed by the same. More particularly, this invention relates to novel methods and compositions or wherein a substantially pure water based composition is provided wherein during the treatment and purification of water based composition, the total dissolved solids are removed from the water based composition and fluoride ions are introduced into the water based composition.

The effectiveness of the fluoride ion in lowering the incidence of dental caries is of major significance to the entire field of dental health. The precise mechanism whereby fluoride reduces tooth decay remains unknown. Innovative avenues of investigation have theorized that structural chemical, physicochemical, electrochemical or thermodynamic mechanisms may be involved; however, at the present time, no single theory adequately explains all the phenomena of dental decay or the precise role which fluoride plays in reducing tooth destruction. Throughout all investigations it has been noted consistently that a direct relationship exists between availability and the uptake of appropriate levels of fluoride and a decrease of an incidence of dental decay. Based on this observation, fluoride administration has evolved as the foremost approach toward providing widespread protection against dental caries.

The levels of fluoride in controlled water fluoridation are so low that there is no danger of ingestion of acutely toxic quantity of a fluoride ion from fluorinated water. It has long been observed that the prevalence of dental caries is low in communities supplied with optimal concentration of fluoride. Much of the early evidence of this fluoride-dental caries relationship was obtained while performing an epidemiological survey. Abundant data are now available from controlled studies in which fluoride was added to water under engineering supervision to substantiate the conclusion that proper adjustment of the fluoride content of the public water supply is an effective and practical caries reducing measure. Approximately one (1) ppm of fluoride in drinking water has been specified as the recommended concentration for partial control of dental decay, however, optimal concentration will vary (0.7 to 1.2 ppm).

Fluoridation of public water supplies has been recognized for many years as an effective and safe way of providing optimal level of the fluoride ion to large segments of population who otherwise may not have an adequate dietary source of fluoride. The addition of fluoride to community drinking water has proven to be the most convenient and effective method of reducing tooth decay on a broad scale. Regrettably, in recent past, it has been estimated that approximately between 35 percent to approximately 40 percent of the population of the United States, particularly adolescents and young adults' generation most susceptible to dental decay have switched to drinking unfluoridated or nonfluoridated, bottled spring water, flavored water, pops, flavored colas, beer, and other processed and packaged mainly water liquids. This trend is annually increasing at an alarming rate, especially in areas where the water supply is scarce or of suspicious and doubtful purity, and the population relies on packaged water for consumption thereby depriving themselves of the optimal level of the dietary source of fluoride.

Still, others may try supplemental fluoridation of "purified" or spring water by individuals. This however has led to a variety of problems, such as: each bottled water must be fluoridated with the exact measured amount of a fluoride supplement which is time consuming and perhaps technical to some people; the amount of fluorides present in the spring water must be known before the supplement is added; unless carefully controlled, the bottled water may be tampered by accidental over fluoridating, and it is costly to purchase the bottled water or flavored water and then to obtain a prescription for the supplemental fluoride from the dentist or the physician.

Untreated waters contain a number of harmful pollutants which give the water color, taste, and odor. These pollutants include viruses, bacteria, organic materials, and soluble inorganic compounds, and these must be removed or rendered harmless before the water can be used again. Sources of contaminated water can be traced to semipublic water systems, municipal water systems, and to individual water systems. The concept of water treatment and water purification consists not only of removal or contaminants from water by varieties of separation processes but also of sterilization and disinfection of pathogenic microorganisms which are small enough to filter through the semipermeable membrane in the separation process. Purification of water cannot be considered complete without both, separation and disinfection, being present in the process or device.

The Environmental Protection Agency has in the past years established maximum contaminant levels of the total dissolved solids not to exceed 500 ppm. These contaminants include organic compounds such as benzene, carbon tetrachloride, methoxychloride, trichlorethylene, trihalomethanes, etc. inorganic compounds such as arsenic, barium, cadmium, calcium, chlorine, chromium, fluoride, iron, magnesium, mercury, lead, nitrate, selenium ,etc.; and radiological contaminants such as dissolved radon.

RELATED ART

Most common methods of physical separation of pollutants from water are:

A. Carbon Adsorption Filter.

Materials such as activated alumina, silica gel, and activated carbon have been developed to adsorb gases, vapors and liquids on their surfaces and organic compounds which may be present in the solution. These materials are porous solids, either in the form of filters or beads, and have unusually high surface development in the form of an ultramicroporous structure, thus possessing a very large internal surface. A fluid, such as water, is able to penetrate through the pore structure of these materials and be in contact with the large surface area available for adsorption. These filters are basically ineffective with microorganisms. However, such filters remove fluoride from water.

B. Ion Exchange.

Water may contain in varying concentrations dissolved salts which dissociate to form charged particles called ions. These ions are positively charged cations and negatively charged anions that permit water to conduct electricity and thus remove ionic species from water and are suited for water treatment and purification for several reasons. First, ionic impurities are removed even when present in rather low concentration. Second, modern ion-exchange resins have high capacities and can remove unwanted ions preferentially. Third, modern ion-exchange resins are stable and readily regenerate, thereby allowing their reuse. This process removes most of the organic and inorganic compounds, including fluoride.

C. Reverse Osmosis.

Reverse osmosis is fundamentally a means of separating dissolved solids from water molecules in aqueous solutions through membranes composed of special polymers which allow water molecules to pass through while holding back most other types of molecules. In this process the feed stream is split into a purified portion (the product water or permeate) and a smaller portion called the concentrate, containing most of the impurities in the feed stream. Most inorganic compounds, such as dissolved fluorides, ferrous iron, chloride, nitrate, and heavy metals such as leads are filtered out in this process.

D. Distillation.

The process of water distillation works by boiling the water then cooling it to condense the stream and collecting the distillate into a container. The advantage of this system of water treatment is that it removes the heavy metals by demineralization and it can also kill certain microorganisms. It is almost ineffective against volatile process and quite expensive. Fluoride is almost completely degraded in boiling the water.

E. Water Softening.

The process of water softening removes calcium and magnesium, hardness minerals, along with iron and lead, and fluoride. It consists of tiny resin beads loosely coated with sodium ions. When hard water flows in, minerals take sodium's place on the resin. The softener periodically reverses its flow, taking salts out of the container to regenerate the resin beads.

F. Iron Removers.

An iron remover uses an oxidizing agent to precipitate the iron and destroys the fluoride through the oxidation-reduction reaction, fluoride being a strong reducer.

Once water is treated by any one, or a combination, of the above methods or processes to separate the organic and inorganic compounds it is essential to treat the water with chemical or physical means in order to destroy the pathogenic viruses, bacteria and other microorganisms before the water is suitable for human consumption. The sterilization or disinfection may be accomplished by any, or combination, of the following methods listed:

A. Nonconventional Treatment Methods.
  1. Electromagnetic Waves.
  2. Sound.
  3. Electron Beams.
  4. Electromagnetism.
  5. Direct and Alternating Currents.
B. Disinfection by Chlorination.
  1. Free Chlorine.
  2. Chloramination.
  3. Chlorine Dioxide.
C. Disinfection with Interhalogens and Halogen Mixtures.
  1. Bromine and Bromides.
  2. Iodine.
D. Ozone Treatment.
E. Potassium Permanganate.
F. Activated Carbon.

The end product of water treatment by separation and disinfection almost certainly will degrade, or completely destroy, the fluoride in the drinking water which is essential in the control of tooth decay. There is no present technology available that will remove all other organic and inorganic dissolved compound yet substantially allow the fluoride ions to pass through a filter or a semipermeable membrane and into the treated water. The process of water treatment functions on the "all-or-none" principle; it will remove all of the contaminants or it will remove none.

There exists a need for a water based composition and method of producing the same which is to be bottled having a relatively stable fluoride ion therein.

SUMMARY OF THE INVENTION

The present invention provides for treatment of water as is generally done during the purification process described above or providing a substantially purified water and then and contemporaneously reintroduces fluoride into the purified water in a manner to maintain the fluoride relatively active for its intended use. This process of fluoridation is best accomplished prior to the bottling of the purified water or immediately at the time of bottling process.

It is an object of the present invention to provide optimal caries inhibition by providing bottled fluorinated pure spring water for individuals living in areas where there is no fluoride naturally present in the water supply or has not been yet implemented.

It is yet another object of the present invention to provide optimal caries inhibition by providing bottled fluorinated water for individuals who for the reasons of their own, be it the unpleasant taste of chemically purified water, such as distinct chlorine taste, or loss of confidence in the purity of the drinking water, have chosen to drink either bottled pure spring water, bottled and flavored pure water or bottled carbonated soda pop or bottled alcoholic and non-alcoholic beverages are thus being deprived from optimal caries inhibition that is normally derived from drinking fluoridated community water but not present in any of the above options.

It is a further object of the present invention to provide optimal caries inhibition by introducing fluoride ions in flavored and carbonated beverages wherein the fluoride ion pH of the composition is at least about 3.0, and preferably between about 3.0 and 3.5, without loss of fluoride potency.

It is yet an additional object of the present invention to provide an aqueous composition of the type stated wherein hydrogen fluoride is present in addition to another fluoride contributing compound and an acid.

It is still further an additional object of the present invention to provide an aqueous composition of the type stated wherein the reaction between the acid and the fluoride ions will not go to completion and the balance between the two ionic substances is maintained at a stable pH range.

It is still another object of the present invention to provide an aqueous composition of the type stated wherein to aqueous composition consists of water, fluorides, flavors, sweeteners, preservatives, buffers (acids having pH of at least about 3.0 and alkalies of pH of at least about 7.5), colors, thickening and emulsifying agents, and other formulating addenda.

It is another further object of the present invention to provide optimal caries inhibition by introducing fluoride ions in flavored and carbonated beverages wherein the fluoride ion concentration is between 0.7 ppm and 1.2 ppm and wherein the pH of the solution is about between 2.5 and 7.0

It is still yet another object of the present invention to provide an aqueous composition of the type stated wherein no more than 50% of the fluoride ions are derived from hydrogen fluoride.

It is still further an object of the present invention to provide an aqueous composition of the type stated wherein the pH stability of the composition is maintained by presence of an acid compound which when dissolved will provide a weak acid and a weak conjugate base.

It is an additional object of the present invention to provide an aqueous composition of the type stated wherein the acidifying agent is a polyprotic acid having the general formula (1) R'R" or (2) $RCO_2H$.

It is also another object of the present invention to provide an aqueous composition of the type stated wherein the aqueous composition is packaged in containers, such as plastic containers, which do not substantially effect pH of solutions contained therein.

It still yet another object of the present invention to provide an aqueous composition of the type stated and a method of making such compositions which can be mass produced inexpensively, efficiently, simply and under controlled conditions.

Other objects and advantages of the present invention will be apparent to those skilled in the art on reading the following disclosure, and therefore, the invention includes the new and novel compositions and processes of making and using the compositions herein illustrated.

Accordingly, the present invention is directed to a bottled fluoridated water based drinking composition for the prevention and control of dental decay, comprising in a substantially non-fluoride reactive bottle containing therein at least one additional fluoride compound selected from a group consisting essentially sodium fluoride, potassium fluoride, magnesium fluoride, calcium fluoride, stannous fluoride, sodium monofluorophosphate, potassium monofluorophosphate and hydrogen fluoride and physiologically acceptable salts thereof, an acidifying compound which when dissolved in water will provide a weak acid and a weak base to initiate a buffering action and prevent the fluoride ions from going to completion and other selected formulating agents to provide protection of tooth surfaces from tooth caries disease and eventual tooth loss.

The water based compositions in the present invention contain a fluoride ion level of about between 0.7 and about 1.2 ppm of which not more than 50 percent is derived from hydrogen fluoride, and a pH of the total composition between about 2.5 and 7.0 provided by a polyprotic acid having the general formulae either (1) R'R" where R' represents more than one hydrogen atom and R" represents an acidic salt radical or (2) a carboxylic acid having the general formula $RCO_2H$, where R represents a carbon atom bonded to a collection of atoms. The compositions of the present invention may contain additional additives such as sweeteners, syrups, flavors, colors, caffeine, carbonating substances, stabilizers, preservatives, alcohols, vitamins, medicaments, emulsifiers, and the like pharmacologically and physiologically acceptable adjuvants.

A polyprotic acid in accordance with the present invention is an acid that contains more than one acidic hydrogen atom, such as sulfuric acid, oxalic acid, sulfurous acid, phosphoric (orthophosphoric) acid, carbonic acid and phthalic acid, and an acid carboxylic acid that contains at least one carbon atom bonded to a collection of atoms, acids such as citric acid, malic acid, galactouronic acid, tartaric acid, oxalic acid, asparagusic acid, propionic acid, benzoic acid, and similar fruit and vegetable products.

Both polyprotic acids donate more than one proton to water or some other base and, since they are weak acids in aqueous solutions their chemical reactions are very similar.

Also, the invention includes a method directed to producing bottled fluoridated water based drinking compositions, comprising the steps of (a) passing a stream of water through a filtering device therein to substantially remove substances in the water therefrom such that upon passing through the filtering device the water is in a substantially purified form, (b) adding to the purified water hydrogen fluoride and at least one fluoride compound selected from a group consisting of sodium fluoride, potassium fluoride, calcium fluoride, stannous fluoride, magnesium fluoride, sodium monofluorophosphate, potassium monofluorophosphate and physiological acceptable salts thereof in a physiologically acceptable amount to provide a fluoridated water capable of providing protection of tooth surfaces from tooth caries; and (c)adding to the purified and fluoridated water a polyprotic compound which is capable of donating protons to water or to a base, compounds such as phosphoric acid and citric acid, and (d) disposing into a nonfluoride reacting bottle the fluoridated water.

DETAILED DESCRIPTION OF THE PREFERRED EMBODIMENTS

Figure 1:
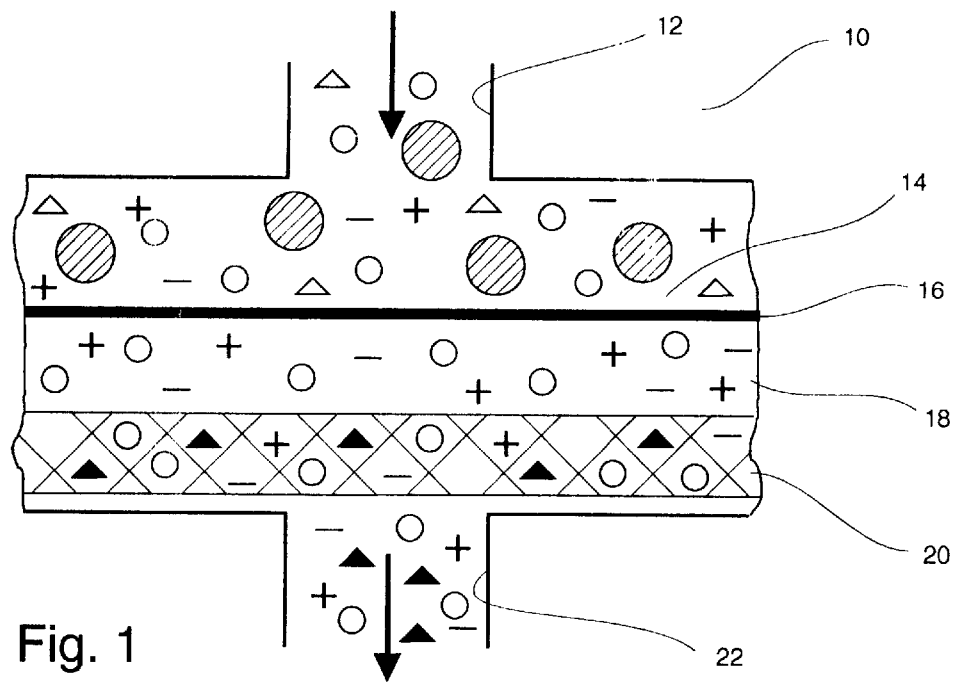

Various investigators have conducted studies to provide sufficient amount of fluoride in liquid compositions to control tooth decay and minimize the effect of fluorosis. Grodberg, U.S. Pat. No. 5,153,005 provides fluoride compounds in liquids, beverage additives, flavored drops of fluoride, etc., Luoma, U.S. Pat. No. 2,230,116, Grigoriev U.S. Pat. No. 2,035,880 and Blaser U.S. Pat. No. 5,182,114 teach of liquid compositions such as beverage, bottled mineral water, fruit juice, etc. to provide concentrates having high contents of fluoride. U.S. Pat. Nos. 4,152,419, 4,425,324, 4,528,181 and British Patent No. 1,435,624 teach fluorosis-free compositions containing binary fluoride sources of sodium fluoride and sodium monofluorophosphate and American Dental Association in the accepted Dental Therapeutics, 38th edition lists liquid acidulated compositions containing an acid, and binary fluoride compounds in high concentrations intended only for rinsing of the oral cavity to control tooth decay. These compositions contain about 2.5 percent sodium fluoride, 0.35 percent hydrogen fluoride and 1.1. percent orthoposphoric acid. Ingestion of these concentrations will cause sublethal symptoms such as nausea, vomiting, abdominal distress, diarrhea, stupor, weakness and lethal symptoms such as muscular weakness, tremors, convulsions, collapse, dyspnea, respiratory and cardiac failure, death. However, I am not aware of anyone suggesting nor am I aware of any literature describing formulating aqueous solutions containing a binary fluoride source, of which one must be hydrogen fluoride, in low concentrations and a polyprotic acid, or acids, in a pH between 2.5 and 7 without the ionic fluoride being exhausted in the acid-base reaction.

The present invention obviates problems of the prior art by providing drinking compositions containing fluoride ions in such low concentrations to prevent undesirable sublethal and lethal effects and yet be in the optimal range of between 0.7 ppm and 1.2 ppm even in presence of a polyprotic acid without affecting the fluoride ion concentration in the compositions. This relative static equilibrium between the hydronium ion ($H_3O^+$) of the weak acid and the hydroxide ion ($OH^-$) of the weak base of the polyprotic acid and the fluoride ions in the solution is achieved by introducing hydrogen fluoride and sodium fluoride (preferably hydrogen fluoride is introduced first since it is a weak acid and sodium fluoride is a base) in the acidulated solution to donate a proton to the weak base of the polyprotic acid thus allow sodium fluoride to retain the full complement of protons in solution.

It is a well known fact in the chemical profession that when a soluble fluoride compound, such as sodium fluoride, is added to water, products are formed until sodium fluoride has been completely used or an equilibrium has been reached. This reaction is described as reaching completion. When sodium fluoride dissolves in water, the major species present are Na⁺ (sodium) plus F⁻ (fluoride) and water A water molecule can be either a proton donor of a proton acceptor, and F⁻ is a base. The reaction can be represented by the equation:

$$H_2O + F^- \leftrightharpoons HF + OH^-$$

This reaction generates hydroxide ions, so the solution is a base. Thus in a solution of sodium fluoride, the fluoride ion (F⁻) is in equilibrium with its conjugate acid, hydrofluoric acid (HF). When a solution of a strong acid, such as phosphoric acid, is added to a salt solution of sodium fluoride, phosphoric acid creates a phosphate buffer of a weak acid ($H_2PO_4^-$) and a weak base ($HPO_4^{-2}$) according to the equation:

$$H_3PO_4 + H_2O \leftrightharpoons H_2PO_4^- + HPO_4^{-2}$$

The buffering action of this solution is created by its weak acid ($H_2PO_4^-$) and conjugate base ($HPO_4^{-2}$). The proton that is transferred is the second proton of $H_3PO_4$ so the appropriate equation becomes:

$$H_2PO_4^- + H_2O \leftrightharpoons HPO_4^{-2} + H_3O^+ \quad (2)$$

This buffering equilibrium remains as long as the amount of hydroxide ions in reaction (1) is less than the total amount of cations present due to the weak acid $H_2PO_4^-$ and hydronium ions $H_3O^+$ represented in reaction (2), however, as fluoride contributes more of its protons to the reaction (2) the pH of the solution begins to rise thus requiring sodium fluoride in reaction (1) to provide additional fluoride protons in an effort to reestablish the buffer equilibrium thus causing virtual consumption of the fluoride ions in the effort.

I have discovered that when hydrogen fluoride salt is dissolved in water, equilibrium is established when only a fraction of the hydrogen fluoride molecules have transferred protons to water molecules thereby preserving the fluoride ions yielded by sodium fluoride in equation (1). The equation of hydrogen fluoride in water is represented by the following:

$$H_2O + HF \leftrightharpoons H_3O^+ + F^- \quad (3)$$

The fluoride ion equilibrium is linked to two other proton-transfer equilibris. The relationship is revealed by combining the proton-transfer equilibrium for hydrogen fluoride (HF) in equation (1) with the proton-transfer equilibrium for the fluoride ion (F⁻) in equation (3):

$$F^- + H_2O \leftrightharpoons HF + OH^- \quad (1)$$

$$HF + H_2O \leftrightharpoons F^- + H_3O^+ \quad (3)$$

$$2H_2O \leftrightharpoons H_3O^+ + OH^- \quad (4)$$

As long as equation (2) remains in constant equilibrium the pH of the composition will remain in acid side, generally between 3.5 and 7 and, likewise, as long as equation (4) is in equilibrium fluoride ions will be constantly present in the composition.

From the foregoing discussion it becomes apparent that fluoride ions in neutral and acid media remain in solution only for a limited time and are very rapidly consumed by the reaction, therefore, it is recommended that a fresh solution be prepared immediately before consumption. However, when hydrogen fluoride, due to its weak acidity, is present in an acid or neutral composition it is readily capable of transferring protons to the water molecule and it does not go to completion, unlike solutions of sodium fluoride wherein fluoride ions are in equilibrium only with its conjugate acid, i.e. hydrofluoric acid (HF) and it will readily go to completion.

The pH of an 0.1N aqueous solution of phosphoric acid is about 1.5 and when diluted with water or when potassium dihydrogen phosphate and anhydrous dihydrogen phosphate are added the aqueous buffered phosphoric acid solution contains $H_2PO_4^-$ as the weak acid and its conjugate $HPO_4^{-2}$ as the weak base and is stable in solution only if the pH is held between the selected range between 2.5 and 7.0, for example pH 5.5. When a weak base such as sodium fluoride is added to this aqueous solution the fluoride protons will accept protons from the weak acid H2P04− thus raising the pH. This reaction will continue until all of the fluoride protons are consumed. However, when a weak acid hydrogen fluoride is added a small fraction of its molecule transfers protons to the aqueous composition and this proton-transfer reaction does not go to completion thus preserving the fluoride ions in solution and stabilizing the pH of the solution, as well.

To prove or disprove the above hypothesis series of experiments were conducted.

Two sets of compositions containing phosphoric acid and fluoride ions were prepared. Set I contained phosphoric acid and sodium fluoride and Set II contained phosphoric acid and hydrogen fluoride and sodium fluoride. The test liquid composition of Set I containing only O2. Mgm was placed in a 200-mL round-bottom flask and diluted to 100-mL with distilled water and shaken to dissolve the sodium fluoride and then 1 gm of phosphoric acid was added and the composition refluxed for five minutes and then set aside to cool. The test liquid composition of Set II contained 1 gm of phosphoric acid in 100-mL of distilled water in a 200-mL round-bottom flask and shaken for about 5 minutes and then 0.1 mgm of hydrogen fluoride was added to the liquid composition and shaken for an additional 5 minutes before 0.2 mgm of sodium fluoride was added and the composition refluxed for five minutes and then set aside to cool. The fluoride ion content was determined with the specific ion electrode as described by L. P. Cancro: Soluble Fluoride Ion Determination. Test Method No. 25 Mar. 11, 1978, and the pH determined by the hydroquinone assay method. The millivolt (MV) readings were compared with a standard curve obtained from analyzing standard fluoride solutions of 0.0, 0.005, 0.05, 0.5, 1.0, 1.5 and 2.0 parts per million (ppm). The readings were taken at the baseline, Day 3, Day 7, Day 14, 1 month, 2 months and 3 months at 40° C. Three months at 40° C. is generally accepted to be equivalent to two years at room temperature. From such accelerated studies, kinetic parameters can be determined and expiration dating estimated. The results are reported in Table I and Table II. The pH of the solutions was 5.5.

TABLE I

| | \multicolumn{7}{c}{Fluoride (ppm)} | | | | | | |
| --- | --- | --- | --- | --- | --- | --- |
| | Baseline | Day 3 | Day 7 | Day 14 | 1 mos | 2 mos | 3 mos |
| Total F from NaF | 2.0 | 1.6 | 1.4 | 1.0 | 0.07 | 0.06 | 0.06 |
| Ionic F | 0.9 | 0.28 | 0.25 | 0.18 | 0.01 | 0.009 | 0.009 |
| % loss of Ionic F | — | 68.89 | 72.22 | 80.00 | 96.89 | 99.00 | 99.00 |

From the above table it is apparent that greatest usage of ionic fluoride in an acidic medium occurs almost instantly upon the dissolution of the fluoride source, and at the 1 month period 98.89 percent of the total ionic fluoride is used in the acid-base reaction leaving only an insignificant amount of fluoride to react with tooth surfaces to effect on dental caries.

TABLE II

| | \multicolumn{7}{c}{Fluoride (ppm)} | | | | | | |
| --- | --- | --- | --- | --- | --- | --- |
| | Baseline | Day 3 | Day 7 | Day 14 | 1 mos | 2 mos | 3 mos |
| F from NaF | 2.00 | 1.80 | 1.45 | 1.32 | 1.00 | 1.00 | 1.00 |
| Ionic F from NaF | 0.90 | 0.81 | 0.76 | 0.74 | 0.70 | 0.70 | 0.70 |
| F from HF | 0.80 | 0.50 | 0.48 | 0.40 | 0.28 | 0.20 | 0.20 |
| Ionic F from HF | 0.75 | 0.47 | 0.39 | 0.31 | 0.30 | 0.30 | 0.30 |
| Total F | 2.80 | 2.30 | 1.93 | 1.72 | 1.28 | 1.20 | 1.20 |
| Total Ionic F | 1.65 | 1.28 | 1.15 | 1.05 | 1.00 | 1.00 | 1.00 |
| % loss Ionic F | — | 22.42 | 30.30 | 36.36 | 39.39 | 39.39 | 39.39 |

Table II clearly indicates that in presence of a polyprotic acid the loss of ionic fluoride occurs mainly from the baseline to Day 3 and thereafter increases slightly until 1 month when an equilibrium is reached. The conclusion therefore is that in binary fluoride aqueous compositions in which one fluoride source is derived from hydrogen fluoride and in which one fluoride source is derived from hydrogen fluoride and in presence of a polyprotic acid, the fluoride compounds retain their respective properties of uptake by the tooth surfaces and fluoride effects on dental caries. The formulations made with hydrogen fluoride and sodium fluoride stabilized with a polyprotic acid in accordance with the present invention are capable of releasing ionic fluoride even in small dosage for combination with dental enamel.

It is an object of the present invention to provide optimal caries inhibition by providing bottled fluoridated pure spring water for individuals living areas where there is no fluoride naturally present in the water supply or has not been yet implemented.

It is yet another object of the present invention to provide optimal caries inhibition by providing bottles of fluorinated water for individuals who for the reasons of their own, be it the unpleasant taste of chemically purified water, such as distinct chlorine taste, or loss of confidence in the purity of the drinking water, have chosen to drink either bottles of pure spring water, bottled and flavored pure water or bottled carbonated soda pop or bottled acholic and non-acholic beverages are thus being deprived from optimal caries inhibition that is normally derived from drinking fluoridated community water but not present in any of the above options.

The present invention used community treated water which has been previously "purified" having dissolved solids exceeding 1,000 ppm. The increase in total dissolved solids from the maximum acceptable levels of 500 ppm to the alarming level of more than 1,000 ppm may be due to possible seepage of hazardous substance into the water pipes through the ground. Most common offenders of hazardous contamination of drinking water were herbicides and pesticides.

The present invention makes ready the water-based solutions by utilizing one or more of the water treatment methods described above to remove the contaminants therefrom. In doing so, fluoride ions, which are essential in the control of tooth decay are also removed. The water is then refluoridated as more fully described hereinafter and bottled in a container which is substantially non-reactive with the fluoride ion contained therein.

Figure 2:
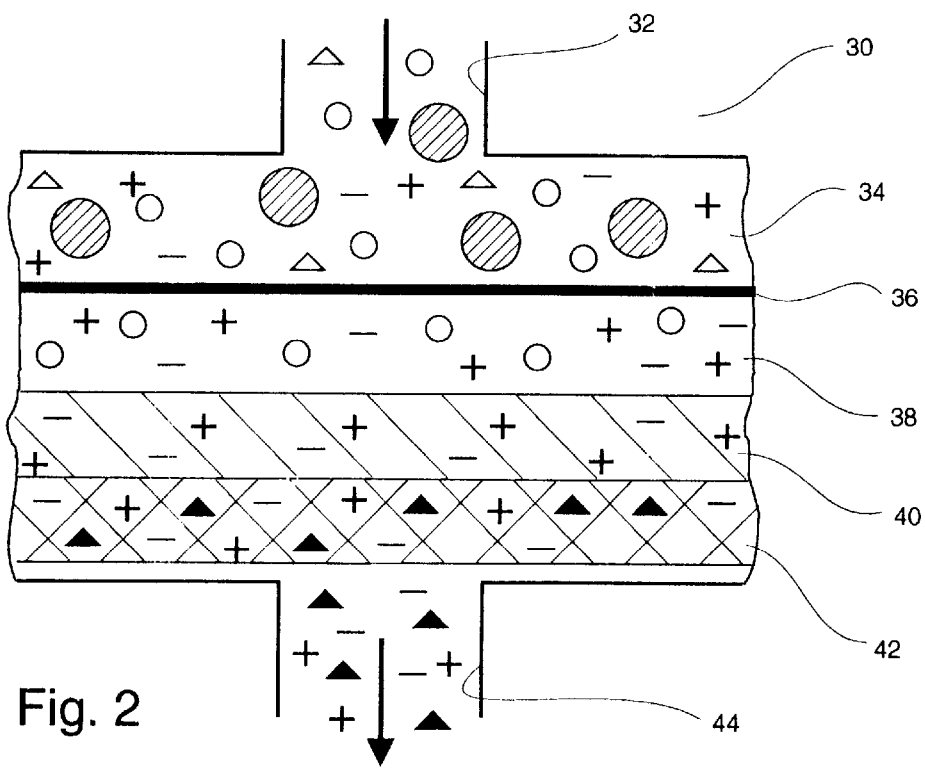
Figures 3, 4:
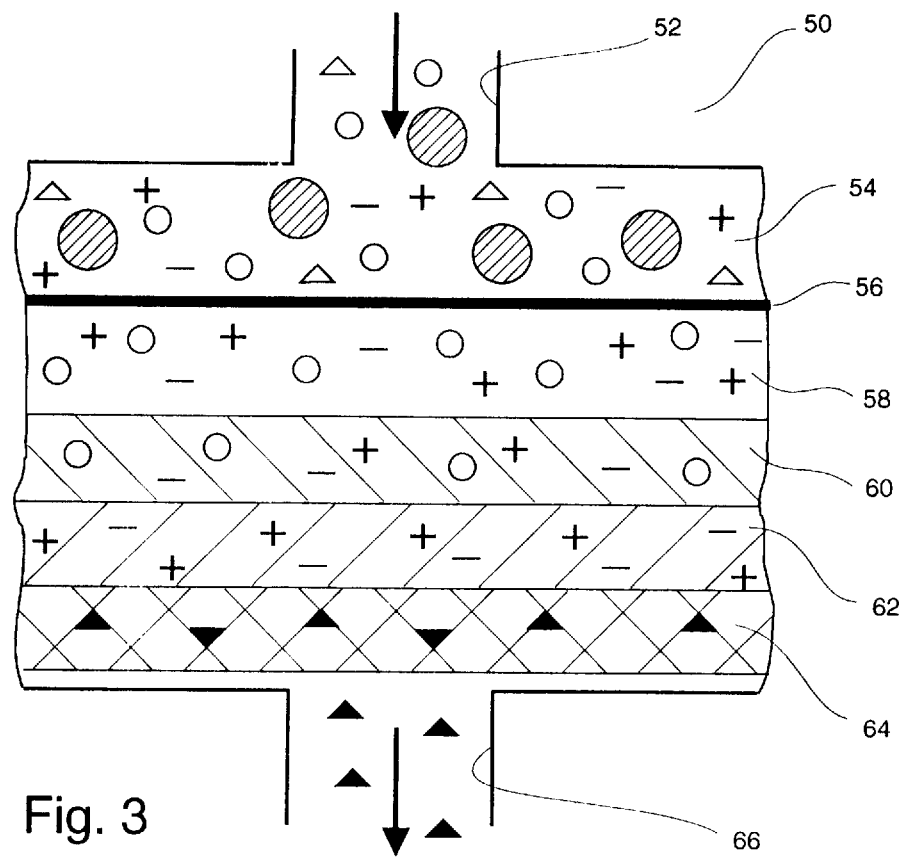

The invention deals with dual function of (a) treatment, purification and partial or complete defluoridation of water and (b) fluoridation of water in one process for control and prevention of tooth decay which uses a cell preferable of plastic material consisting in one embodiment of the following:

(1) As shown in FIG. 1, a cell 10 has an inlet 12 through which water passes into the cell 10, a reverse osmotic chamber 14, a semipermeable membrane 16, another reverse osmotic chamber 18, fluoride supply chamber 20 and an outlet 22;

(2) As shown in FIG. 2, a cell 30 has an inlet 32 through which water passes into the cell 30, a reverse osmotic chamber 34, a semipermeable membrane 36, another reverse osmotic chamber 38, carbon filter 40, fluoride supply chamber 42 and an outlet 44; or (3) As shown in FIG. 3, a cell 50 has an inlet 52 through which water passes into the cell 50, a reverse osmotic chamber 54, a semipermeable membrane 56, another reverse osmotic chamber 58, carbon filter 60, ion exchange 62, fluoride supply chamber 64 and an outlet 66. FIG. 4 shows a legend of symbols as depicted in FIGS. 1–3.

The carbon filter preferable has a total surface area range of 450 to 1800 m2/gram and made up of either granular pellets or powder through selective affinity for nonpolar molecules for nonpolar molecules absorb the organic compounds, (such as dissolved chemicals, solvents, pesticides and chlorine that have passed through the semipermeable membrane but adhere to the hydrophobic surfaces of the multiple macro pores and micro pores of the activated carbon granules).

The ion exchange preferably includes a bed of tiny resin beads loosely coated with sodium ions, usually sodium zeolite, positioned below the activated carbon filter, which remove the hardness ions, such as calcium, magnesium, lead and iron ,from the filtrate through the ion-exchange process, i.e., the sodium ions from the solid phase are exchanged with the hardness ions from the aqueous phase that have small enough molecules to filter through the semipermeable membrane in the reverse osmosis process and polar in solution so that they are not affected by the activated carbon filter.

The fluoridation supply consists of either dry composition or solution of a suitable fluoride compound which when exposed to the purified water after the completion of the treatment process will provide between 0.7 to about 1.2 ppm of fluoride.

Water flow through the cells is maintained under weight pressure of approximately 250 pounds per square inch to force only water molecules and some dissolved organic and inorganic molecules while holding back most other types of molecules including and most inorganic salts. The water filtrate of the present invention contains water and less than about 200 ppm total dissolved solids with more than 95% of the dissolved organic and inorganic compounds and heavy metals being removed during the treatment processes. Fluoride, being ionic in nature and of relatively large ceases prevented from passing through the selective semipermeable membrane of the reverse osmosis process and only about less than 15% is able to pass, the remainder of which is substantially removed either by the active carbon filter or the ion exchange process. Therefore, in order to be effective in a dental health pursuance of tooth decay control, fluoride must be reintroduced in the drinking water composition.

Fluoride feeders may be employed with the present invention to proportion a given amount of fluoride into purified or treated water. Two of the most suitable in the present invention are a) Automatic and b) Manual.

A. Automatic.
1. Solution feeders, which are essentially small pumps, feed a carefully measured quantity of accurately prepared fluoride solution during a specific time; and
2. Dry feeders are devices which deliver a measured quantity of the solid material during a given time interval.

There are varieties of dry feeders such as gravimetric dry feeder, volumetric dry feeder piston or centrifugal pump and diaphragm pump.

B. Manual.

The selected source of a fluoride donor may be either solution or dry fluoride compound or salt and it may be added to a specific amount of purified water in a measured amount. However, the disadvantages of the manual system of fluoridation are many fold, i.e., they:

1. must be reliable and accurate of feeding fluoride, with particular reference to the incorporation of means to prevent overdosing;
2. must provide safeguards of tampering or accidental adding of harmful chemicals;
3. must provide provisions for monitoring the fluoride level in purified water and for replenishment of the fluoride source; or
4. involve human errors.

A described method of refluoridation of water in the present invention is best accomplished by selecting a fluoride salt or compound which is relatively water insoluble when applied in the process of the present invention. In order to determine which fluoride compound is the most suitable in the concept of the present invention, several sources of fluoride were tested to determine their relative solubilities in a measured amount of water. Ten grams of each compound were weighed and then dissolved in 100 ml of water without stirring but the beakers were gently swirled and the time taken. The relative particle size in microns was recorded prior to the start of the test for each compound and also recorded. The percent of fluoride ions in the pure compounds were obtained from Merck Index and Accepted Dental Therapeutics. In accordance with the present invention, solubility of a compound is defined as "the maximum amount of a substance that can be dissolved in a given amount of solvent, usually expressed as the mass volume of solute in a unit mass or volume of solvent at a given temperature." Table III illustrates the results of the test.

TABLE III

Characteristics of Fluoride Compounds

| Compound | Fluoride ion % 100% pure material | Solubility (g per 100 g H20) at 25 C. | Relative particle size micron |
|---|---|---|---|
| Calcium Fluoride | 48.8 | 0.0016 | 1 |
| Sodium Silicofluoride | 60.7 | 0.762 | 1 |
| Sodium Fluoride | 45.25 | 4.05 | 1 |
| Hydrofluorosilicilic acid | 79.2 | Infinite | Liquid |
| Magnesium silicofluoride | 41.5 | 64.8 | 6 |
| Ammonium Silicofluoride | 63.9 | 18.5 | 7.5 |
| Potassium fluoride (hydrous) | 20.2 | 100 | 5 |
| Stannous fluoride | 24.25 | 30 | 1 |
| Sodium monofluorophosphate | 12.58 | 45 | 4 |

Table III demonstrates that Calcium Fluoride is the least water soluble and hydrous, Potassium Fluoride is the most soluble of the dry compounds that were selected for the test.

All of the compounds listed above might be used as a source of fluoride in refluoridation of the treated water. An additional test was conducted using a variety of relative particle sizes to form the refluoridation cartridge and inserting the refluoridation cartridge into the cell of the water treatment device as described above to determine which particle size will provide 1 ppm of fluoride into purified water when exposed to a constant and controlled stream of water that has a contamination level of more than 1,000 total dissolved solids.

For this experiment, eighteen cartridges were prepared. Each cartridge was 5 inches in diameter and 1.5 inches thick and made of permeable filter or membrane, of cellulose resin material with multiple micro pores (0.25 microns) and about 5 mil thickness. Inside the hollow center of the cartridge variety of relative particle sizes of the fluoride compounds used in the experiment were packed with the smallest size of the powdery fluoride compound (0.5 microns) being larger than the permeable micro pores (0.25 microns). The weight of the fluoride compound was 100 grams in each cartridge.

For purposes of this phase of the experiment, only Calcium Fluoride and Sodium Fluoride were used in this experiment because Calcium Fluoride is the least soluble of all preferred fluoridating compounds and Sodium Fluoride is the least soluble of all Sodium containing fluoride salts and compounds.

The object of the experiment was to find which of the two compounds, Calcium Fluoride or Sodium Fluoride, and at what relative particle size will provide 1 ppm of fluoride when the inflow rate of 250 ml of water per minute was kept constant. The municipally treated water was passed through the purification method described above in addition to the refluoridation cartridge which was inserted into the filtration cell prior to each test run.

TABLE IV

Relative Particle Size and the Solubility of the Selected Fluoride Compounds

| SAMPLES FLUORIDE | PARTICLE SIZE | ppm FLUORIDE/250 ML PER MINUTE | |
| --- | --- | --- | --- |
| | | CALCIUM FLUORIDE (SAMPLE A) | SODIUM (SAMPLE B) |
| 1 (a,b) | 0.5 micron | 3.02 | 40.95 |
| 2 (a,b) | 10 micron | 2.96 | 32.45 |
| 3 (a,b) | 50 micron | 2.15 | 26.75 |
| 4 (a,b) | 150 micron | 1.85 | 15.12 |
| 5 (a,b) | 10 mm | 1.35 | 12.30 |
| 6 (a,b) | 50 mm | 1.0 | 8.15 |
| 7 (a,b) | 75 mm | 0.5 | 6.05 |
| 8 (a,b) | 125 mm | 0.002 | 4.75 |
| 9 (a,b) | 200 mm | 0.0009 | 1.00 |

From this experiment it was discovered that granular Calcium Fluoride of approximately 50 millimeters in diameter and under the constant inflow of water at a rate of 250 ml per minute will dissolve sufficient amount of fluoride ions of about 1.0 ppm, whereas if Sodium Fluoride is desired to be utilized as the fluoride ion donor the size of the particles should be compressed under heat and pressure into a marble-like shape having the diameter of at least 200 millimeters.

Because fluoride-bearing minerals are so widely distributed over the earth, it would be expected that water containing fluorides would also be found almost anywhere, even in spring and well water. As more data became available on the large number of water supplies containing fluorides, it became evident that a large number of people have been drinking water containing fluorides and that the severity of tooth decay lesions and of mottling of enamel varied with the fluoride level of the water. Although some of the general public consumes water derived from spring source and consider it to be "pure", the amount of fluorides, or absence, cannot be determined unless chemical analysis is undertaken. Voluminous studies to determine the amount of fluorides in the local water supplies have been conducted to confirm the presence or absence of fluoride and it was concluded beyond any doubt that areas of ground fluorides vary from locality to locality. It appears that the way to ensure the presence of optimal levels of fluorides in the drinking water would be to either (a) analyze each source of water and then add or remove the amount of fluorides in sufficient quantity to provide the optimal level, or (b) to remove completely any presence of fluorides from the water source and then under controlled conditions add the appropriate amount of fluorides to provide the optimal level. In accordance with the present invention it was discovered that the principle of water purification to remove hazardous dissolved contaminants together with the fluoride and then add the proper amount of fluorides under controlled conditions is sound.

The present invention provides methods and processes for a single step of treatment of drinking water to a level wherein the maximum contaminants of the total dissolved solids does not exceed about 500 ppm and wherein the treated water from which fluorides have been removed during the treatment and purification process are replenished by the addition of fluoride compounds or solutions of fluoride compounds in sufficient amounts to provide fluoride ions in the water solutions from about 0.7 ppm to about 1.2 ppm with respect to the total composition of the potable water.

The methods of refluoridation is accomplished by providing preferably a removable and replaceable cartridge made of micro porous resinous material and containing therein the fluoride compound, either a dry or a liquid state, which fluoride compound may be dependent upon its solubility potential to release only sufficient fluoride to provide between from about 0.7 to 1.2 ppm in the water composition when an adjusted and constant flow of water filters through the cartridge or the cartridge may release a predetermined amount of preferably liquid fluoride composition when a given volume of the treated water filters through the cartridge and into a container. The refluoridation cartridge may be such that it can be attached to any of the existing water treatment devices or it may be built into the water treatment device as one integral unit. In accordance with the present invention, the refluoridation or fluoridation if pure spring water is used is positioned at the end of the water treatment process.

The drinking solutions of the present invention are made by dispersing a selected amount of fluoride salt (the fluoride ions should be approximately between 0.7 and up to 1.2 p.m. of the final total composition of the solution) in water that has not been exposed to a purification process and obtained directly from natural spring wherein dissolved are sweeteners, flavoring agents, thickening and emulsifying agents, preservatives, alcohols, coloring agents, carbonating and effervescing agents, syrups, acids and/or alkalies (the final pH of the composition not less than about 2.5), natural juices and other formulating and manufacturing aids. Furthermore, the spring pure drinking solutions of the present invention may contain only fluoride in its final composition or it may contain fluoride and one or more of the selected pharmacological and physiological aids. All of the ingredients in the present invention are selected from those that are physiologically and chemically tolerable with reference to the particular utility of the invention and must be compatible with one another and especially with the fluoride salt. The ingredients may either be solid, crystalline, powder, gel, semi-solid or liquid and must be water soluble. It has been found in connection with the present invention that the most suitable aqueous compound for fluoride dissolution is pure spring water.

For the effective results the fluoride compounds are present in an operative range in an amount of from about 0.15 ppm to about 5.0 ppm by weight with respect to the total weight of the drinking water and preferably in an operative range in an operative range in an amount of from between about 0.7 ppm to about 1.2 ppm with respect to the total weight of the drinking water composition.

The aqueous compositions produced in accordance with the present invention consist of fluoridating agents that are pharmacologically and physiologically innocuous when used in the suggested amounts. The fluoridating agents are selected from a group comprising sodium fluoride, stannous fluoride, monofluorophosphate, hydrogen fluoride, calcium fluoride, sodium silicofluoride, hydrofluorosilicilic acid, magnesium silicofluoride, ammonium silicofluoride, potassium fluoride, and similar fluoride containing substances that are capable of liberating fluoride ions when dissolved in an aqueous solution, such as water.

The sweetener is added to the composition in an amount to lend a desirable sweet taste to the composition and will vary depending on the types and amounts of fluorides and other formulating agents which are added to the subject drinking water compositions. In most cases the sweetener may normally be present in an operative range of about 0.005 percent to about 20.5 percent by weight with respect to the final total weight of the water composition and preferably in an operative range in an amount between 0.5 percent to about 1.5 percent with respect to the total weight of the drinking water composition. Examples of the sweetening agents that can be used in accordance with the present invention are selected from a group consisting of saccharine, sodium saccharine, potassium saccharine, aspartame, xylitol, sorbitol, sodium cyclamate, glycerol and sugar and mixtures thereof.

The fluoridated drinking water compositions of the present invention may contain flavoring agents that are pharmacologically and physiologically nontoxic when used in the suggested amounts. The flavoring agents comprise a member of a group consisting of substances which are liquids, powders, gels, crystals or other substances made by a process of synthesis or similar artifice, extracted, isolated, or otherwise derived, with or without intermediate or final change of identity, from a vegetable, plant, animal, mineral or other source that, when added or applied to the drinking water compositions, is capable of imparting a flavor thereto. Examples of flavoring agents which can be used in the fluoridated drinking water compositions of the present invention are essential oils such as anise oil, cinnamon oil, clove oil, menthol, natural and synthetic substances such as grape, lime, mint, chocolate, lemon, strawberry, cherry, etc., and mixtures thereof. In most cases the flavoring agent or mixtures will normally be present in an operative range of about 0.05 percent to about 25 percent by weight with respect to the total weight of the composition.

Examples of acidifying agents that can be used in accordance of the present invention of fluoridated drinking water to lower the pH and to provided tartness of the compositions, when desired, may be present in an amount to maintain operative range of pH from about approximately 2.5 to about 7.0 and are compounds that can yield hydrogen ions or protons in solution. Such compounds are for example orthophosphoric acid, citric acid, acetic acid, boric acid, and other like compounds and mixtures thereof.

The carbonation of the fluoridated drinking water compositions of the present invention may be accomplished by several methods available commercially to those knowledgeable in the arts such as introducing carbon dioxide (carbonic acid gas, carbonic anhydride) under high pressure and low temperature, by the fermentation of glucose, or by dropping acid on a carbonate: $CaCO3+H2SO4+CaSO4+CO2$.

Examples of preservatives which can be used in the fluoridated drinking water compositions of the present invention are methylparaben, propylparaben, phenylmercuric nitrate, sodium bisulfite, sodium nitrite, sodium benzoate, benzoic acid, chlorobutanol, ethylenediaminatetracitic acid (EDTA), thimerosal, phenylmercuric acetate, disodium calcium EDTA, etc, and mixtures thereof. In most cases the preservative will normally be present in an operative range of about 0.05 percent to about 5 percent by weight with respect to the total weight of the composition.

Examples of thickening and emulsifying agents that are preferred substances that meet the requirements of the present fluoridated spring drinking water compositions are mucilaginous substances selected from the group consisting of acacia, bentonite, carrageenan moss extractive of sodium, potassium and calcium salt, methyl cellulose, sodium carboxymethyl cellulose, hydroxyethylcellulose, hydroxypropylcellulose and the salts of sodium, calcium and potassium of the cellulose compounds, magnesium aluminum silicate, silica acrogel, gelatin and gelatin derivatives of which gelatin is the main radical, hydrolyzed polyvinyl acetate, hydrolyzed cellulose esters such as cellulose acetate hydrolyzed to an acetyl content of 19 to 26 percent, polyvinyl alcohol, a vinyl alcohol polymer containing urethane carboxylic acid groups, polyethylene oxide, colloidal albumen, naturally occurring or synthetic alginates such as salts of water soluble metals of sodium, potassium and magnesium, polyethylene glycols, propylene glycol alginates, etc. Various combinations of gelling or nongelling agents and activators such as sterculia gum, tragacanth, starch, guar gum and xanthin gum, and mixtures thereof may be used. The concentration of the thickening and emulsifying agent which may be used in the compositions of the present invention is present in the amount from about 0.00 percent to about 10 percent by weight with respect to the weight of the total weight of the composition.

The most advantageous coloring agents for use in the fluoridated drinking water of the present invention are food, drug and cosmetic color additives that are presently certified under the Food, Drug & Cosmetic Act including dyes and colors such as FD & C and D & C red, yellow, green, blue, orange and aluminum and calcium lakes thereof may be used. It must be understood that multiple combinations of colors may be employed to obtain the desired hue of the final composition or the fluoridated drinking water compositions may be desired to be allowed to remain its natural colorless state without artificial coloration.

The fluoridated spring drinking water compositions produced in accordance with the present invention may generally have only from about 0.15 ppm to about 5.0 ppm of fluoride in its final composition or it may generally have components specified herein in the amounts from about 0.005 to about 20.5 percent sweetening agent; from about 0.05 percent to about 25 percent flavoring agents, from about 0.05 percent to about 5 percent preservatives; from about 0.00 percent to about 10 percent thickening or emulsifying agents; sufficient amount of acid to provide desired tartness and to maintain pH from about 2.5 percent to about 8.5 percent, a sufficient amount of carbonating gas or substances to provide desired carbonation and effervescence. It must again be understood that the final fluoridated drinking water composition may only contain fluoride and no other additive or it may contain additional one or more additives without departing from the nature and principle of the invention.

EXAMPLES

In order to point out more fully the nature of the present invention, the following specific examples are given as an illustrative embodiment of the process and compositions produced thereby.

Example 1

To 1,000,000 ml. of water 2.2 mg. sodium fluoride*, 0.6 mg hydrogen fluoride and 9,000 mg. Orthophosphoric acid were added and completely dissolved before packaged into plastic containers. The composition contains the following:

|  | Weight/Volume |
| --- | --- |
| Water | 1,000,000 ml. |
| Sodium Fluoride | 2.2 mg. |
| Hydrogen Fluoride | 0.6 mg. |
| Orthophosphoric Acid (Phosphoric Acid) | 9,000.0 mg. |

* 2.2 mg. sodium fluoride contains 1 mg. fluoride ion. The pH of this composition is between 3.0 and 3.5.

Example 2

A flavored drinking water was prepared containing the following:

|  | Weight % |
| --- | --- |
| Sodium fluoride | 0.00022 |
| Water, spring pure | 97.19168 |
| Hydrogen Fluoride | 0.00010 |
| Citric Acid | 0.98 |
| Strawberry Flavor | 1.25 |
| Sodium Saccharine | 0.20 |
| Sodium Benzoate | 0.40 |
| FD & C Red #40 | 0.008 |

Example 3

A carbonated beverage composition was prepared containing the following:

|  | Weight % |
| --- | --- |
| Hydrogen Fluoride | 0.00010 |
| Sodium fluoride | 0.00022 |
| Water, purified | 59.78 |
| Sodium Carbonate | 12.45 |
| Orthophosphoric Acid | 1.00 |
| Citric acid | 0.55 |
| Blueberry syrup | 25.55 |
| Sodium saccharine | 0.23 |
| Preservative | 0.43 |
| FD & C Red #40 | 0.006 |
| FD & C Blue #2 | 0.002 |

This composition has a pH of about 5.2
* Blueberry syrup was prepared by adding 5.55 ml. of blueberry flavor into 12.00 ml pure spring water and 8.00 ml. of glycerol. This composition has the ph 5.6.

Example 4

A carbonated beverage composition was prepared containing the following:

|  | Weight % |
| --- | --- |
| Sodium fluoride | 0.00028 |
| Hydrogen Fluoride | 0.00009 |
| Orthophosphoric Acid | 0.98 |
| Water, carbonated, spring pure | 71.77 |
| High fructose corn syrup | 18.96 |
| Caffeine | 0.94 |
| Sucrose caramel color | 6.35 |
| Kola flavor | 0.65 |
| Preservative | 0.35 |

Example 5

A flavored beverage was prepared containing the following:

|  | Weight % |
| --- | --- |
| Stannous fluoride | 0.0004* |
| Hydrogen Fluoride | 0.0002 |
| Water, carbonated, spring pure | 79.18 |
| Citric acid | 3.85 |
| Lime flavor | 0.86 |
| Orange flavor | 0.82 |
| Sodium citrate | 2.25 |
| Vitamins | 12.45 |
| Preservative | 0.36 |
| Sweetener | 0.22 |
| FD & C Yellow #5 | 0.008 |
| FD & C Blue #1 | 0.0015 |

*4.0 mg. stannous fluoride yield 1.0 mg. fluoride ions.

* 4.0 mg. stannous fluoride yield 1.0 mg. fluoride ions.

Example 6

A flavored spring pure drinking water was prepared containing the following ingredients:

|  | Weight % |
| --- | --- |
| Sodium monofluorophosphate | 0.00076* |
| Hydrogen Fluoride | 0.00036 |
| Phosphoric Acid | 0.99 |
| Citric Acid | 0.50 |
| Xylitol, sweetener | 0.52 |
| Propylene Glycol Alginate | 0.41 |
| Sodium Benzoate | 0.38 |
| FD & C Red #40 | 0.008 |
| FD & C Blue #1 | 0.0003 |
| Water, purified | 97.03 |

*7.6 mg. sodium monofluorophosphate yield 1.0 mg. fluoride ions.

* 7.6 mg. sodium monofluorophosphate yield 1.0 mg. fluoride ions.

Example 7

A drinking water composition was prepared containing the following:

|  | Weight % |
| --- | --- |
| Stannous fluoride | 0.0804 |
| Hydrogen Fluoride | 0.0350 |
| Phosphoric Acid | 1.00 |
| Water, spring pure | 98.88 |

Example 8

A flavored beverage was prepared containing the following:

|  | Weight % |
| --- | --- |
| Sodium fluoride | 0.000154 |
| Citric acid | 4.15 |
| Flavor | 1.05 |
| Preservative | 0.45 |
| Sweetener | 0.18 |
| Thickeners | 0.005 |

-continued

|  | Weight % |
|---|---|
| Colors | 0.003 |
| Water, carbonated, spring pure | 94.16 |

This composition was prepared by dissolving Citric Acid, flavor, preservative sweetener, thickener and color into the carbonated water and stirred until completely in solution. Sodium Fluoride was then added in the composition with continuous stirring for about 10 minutes, The final pH of the composition was found to be 2.0 with quinhydrone assay and the concentration of fluoride ion 0.7 ppm. with colorimetric titration method. The composition was allowed to remain closed in a plastic bottle for one week and then again the pH and fluoride ion concentration measured with the above methods. It was found that the pH rose slightly to 2.1 and the fluoride ion dropped to 0.5 ppm. Four weeks from the base line, the determinations were again taken and it was discovered that the pH rose to 2.2 and the fluoride ion concentration dropped to 0.3 ppm. and after eight weeks the results were 2.2 pH and 0.15 ppm. concentration.

Example 9

A flavored beverage was prepared containing the following:

|  | Weight % |
|---|---|
| Sodium fluoride | 0.000154 |
| Hydrogen Fluoride | 0.00007 |
| Citric acid | 4.15 |
| Flavor | 1.05 |
| Preservative | 0.45 |
| Sweetener | 0.18 |
| Thickeners | 0.005 |
| Colors | 0.003 |
| Water, carbonated, spring pure | 94.16 |

This composition was prepared similarly to Example 8 with the addition of Hydrogen Fluoride. The final pH of the composition was found to be 2.0 with quinhydrone assay and the concentration of fluoride ion 0.7 ppm. with colorimetric titration method. The composition was allowed to remain closed in a plastic bottle for one week and then again the pH and fluoride ion concentration measured with the above methods. It was found that the pH and the fluoride ion remained the same. After four weeks and eight weeks from thebase line, the pH and the fluoride ion remained the same.

The invention provides a method for making bottled drinking water compositions which provide fluoride for the control and prevention of dental caries development comprising preferably pure spring water or filter-purified water and (a) water soluble or water miscible fluoride yielding compound, (b) hydrogen fluoride in concentration of not more than 50% of the concentration of the fluoride yielding compound and (c) a polyprotic acid containing more than one acidic hydrogen atom, in such concentrations that they will provide optimal protection against dental caries.

The invention also provides a method for making a some bottled fluoridated drinking compositions which when taken internally provide optimal protection against tooth decay comprising water and pharmaceutically and chemically compatible harmless formulating aids selected from a group consisting if sweetening agents, flavoring agents, preservatives, thickeners and/or emulsifiers, syrups, alcohols, caffeine, colorants, vitamins, carbonating agents, and other suitable additives and mixtures thereof wherein water and fluoride must be a part of the composition.

The invention further provides a method for making fluoridated drinking bottled water compositions wherein pharmacologically and physiologically harmless pharmaceutical and chemical aids are being added in innocuous amounts within the following range percent by weight based on the total weight of the composition: (a) fluoride compounds or salts, 0.15 ppm and preferably between 0.7 and 1.2 ppm; (b) hydrogen fluoride, to provide not more than 50% of the total fluoride ions in the composition; (c) polyprotic acid, to maintain the pH between 3.6 and 7.0; (d) sweetening agents, 0.005 to about 20.5 weight percent; (e) flavoring agents, 0.05 to about 25 weight percent; (f) preservatives, 0.05 to about 5.0 weight percent; (g) thickeners and/or emulsifiers, 0.00 to about 10 weight percent; (h) syrups, 0.00 to about 80.0 weight percent; (I) alcohols, 0.00 to about 25.0 weight percent; (j) caffeine, 0.0 to about 10.0 weight percent; (k) colorants, 0.00 to about 5.0 weight percent; (l) vitamins, as desired; (m) carbonating agents, 0.00 to about 75.0 weight percent and other equally harmless formulating and compounding aide which neither contribute to the taste and flavor nor to the texture of the desired compositions.

In view of the above disclosure, it will be noted that the several objectives of the invention are achieved and other advantageous results obtained, therefore, what I desire to claim and secure by Letters Patent is:

1. A bottled fluoridated carbonated flavored water based drinking composition for the prevention and control of dental decay, comprising:

in a substantially non fluoride reactive bottle, a continuous phase of water containing therein (a) hydrogen fluoride, (b) at least one fluoride yielding compound selected from a group consisting essentially of sodium fluoride, potassium fluoride and magnesium fluoride, sodium monofluorophosphate, potassium monofluorophosphate and magnesium monofluorophosphate, stannous fluoride, calcium fluoride, sodium silicofluoride, hydrofluorosilicic acid, magnesium silicifluoride, ammonium silicofluoride wherein there exists a weight ratio of between about fifty percent or less concentration of (a) to (b), and c a polyprotic acid selected from a group consisting of phosphoric (orthophosphoric) acid, citric acid, sulfuric acid, in physiologically acceptable amounts which maintain a pH concentration in the range of between 2.5 and 7.0, (d) a flavoring agent, and (e) a carbonating substance.

2. The bottled fluoridated carbonated flavored water based composition of claim 1, wherein total fluoride ion concentration is in an amount from about 0.7 ppm to 1.2 ppm.

3. The bottled fluoridated carbonated flavored water based composition of claim 1, wherein said fluoride yielding compound (b) includes sodium fluoride.

4. The bottled fluoridated carbonated flavored water based composition of claim 1, wherein said concentration is between about 0.5 to 0.25 of (a) to (b).

5. The bottled fluoridated carbonated flavored water based composition of claim 1, wherein said composition further includes one of a pharmacologically and physiologically harmless compounds selected from a group consisting of a sweetening agent, a preservative, a syrup, a colorant, an alcohol, a thickener and emulsifier, a caffeine, a vitamin and mixture thereof.

6. The bottled fluoridated carbonated flavored water based composition of claim 1, wherein said bottle is of a plastic material.

* * * * *